US009221837B2

(12) United States Patent
Himmler et al.

(10) Patent No.: US 9,221,837 B2
(45) Date of Patent: *Dec. 29, 2015

(54) PROCESS FOR PREPARING DITHIINE-TETRACARBOXIMIDES

(75) Inventors: Thomas Himmler, Odenthal (DE); Frank Volz, Köln (DE); Thomas Geller, Odenthal (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/225,411

(22) Filed: Sep. 3, 2011

(65) Prior Publication Data

US 2012/0226052 A1 Sep. 6, 2012

Related U.S. Application Data

(60) Provisional application No. 61/381,163, filed on Sep. 9, 2010.

(30) Foreign Application Priority Data

Sep. 3, 2010 (EP) .................................... 10175181

(51) Int. Cl.
C07D 495/14 (2006.01)
(52) U.S. Cl.
CPC .................... C07D 495/14 (2013.01)
(58) Field of Classification Search
None
See application file for complete search history.

(56) References Cited

U.S. PATENT DOCUMENTS

| 3,364,229 | A | 1/1968 | Draber et al. | |
|---|---|---|---|---|
| 8,450,360 | B2* | 5/2013 | Himmler et al. | 514/411 |
| 2010/0120884 | A1 | 5/2010 | Seitz et al. | |
| 2011/0257411 | A1 | 10/2011 | Himmler | |
| 2011/0269973 | A1* | 11/2011 | Himmler et al. | 548/431 |
| 2011/0275831 | A1 | 11/2011 | Lui et al. | |
| 2011/0319462 | A1* | 12/2011 | Seitz et al. | 514/411 |
| 2012/0022270 | A1 | 1/2012 | Himmler et al. | |

FOREIGN PATENT DOCUMENTS

| JP | 10-251265 A | 9/1998 |
|---|---|---|
| PL | 143 804 B2 | 11/1988 |
| WO | WO 2010/043319 A1 | 4/2012 |

OTHER PUBLICATIONS

Ooi et al., Recent advances in asymmetric phase-transfer catalysis. Angewandte Chemie International Edition, 2007, 46, 4222-4266.*
Mastracchio, A. Phase-transfer catalysis. MacMillan Lab Group Meeting (power point presentation), Apr. 10, 2008, 1-53.*
Quintanar-Guerrero et al. Pseudolatex preparation using a novel emulsion-diffusion process involving direct displacement of partially water-miscible solvents by distillation. International Journal of Pharmaceutics, 1999, 188, 155-164.*
Esikova, I.A., Handbook of Phase Transfer Catalysis. Ed. Y. Sasson and R. Neumann. 1st ed. London: Chapman & Hall, 1997. Print.*
Brisse, F., et al. "N,N'-Dimethyl1-1,4-dithine-1,2:4,5-tetracarboximide and N,N'-dimethyl-1,4-diselenine-1,2:4,5-tetracarboximide," *Acta Crystallogr.* C56:190-192, International Union of Crystallography, United States (2000).
Gülten, S. "The Synthesis and Characterization of Solvatochromic Maleimide-Fused N-Allyl- and N-Alkyl-Substituted 1,4-Dithiines and Diels-Alder Reactions with Anthracene," *J. Heterocyclic Chem.* 47:188-193, HeteroCorporation, United States (2010).
Hayakawa, K., et al. "Reagent Design and Study of 1,4-Dithiins as a Promising Class of Reagents (Synthons) for Cycloaddition. Diels-Alder Reactions with Anthracene Derivatives via Charge-Transfer Complexes," *J. Am. Chem. Soc.* 104:7136-7142, American Chemical Society, United States (1982).
Katritzky, A. R., and Fan, W.-Q., "Some Novel Quinone-Type Dyes Containing Naphthoquinone and Related Fused Ring Systems," *J. Heterocyclic Chem.* 25:901-906, Journal of Heterocyclic Chemistry, United States (1988).
Valla, A., et al. "Atypical Oxidation Reaction by Thionyl Chloride: Easy Two-Step Synthesis of N-Alkyl-1,4-dithiines," *Synthetic Communications* 36:3591-3597, Taylor & Francis Group, LLC, United States (2006).
Yun, J. Y., et al. "Quantitative regio-selective Diels-Alder reaction of an unsymmetrical 1,4-dithiin and anthracene through heterogeneous solid state conversion," *Dyes and Pigments* 83:262-265, Elsevier Ltd., Netherlands (2009).
Zentz, F., et al., "Syntheses, in vitro antibacterial and antifungal activities of a series of N-alkyl, 1,4-dithiines," *Il Farmaco* 60:944-947, Elesevier SAS, France (2005).
International Search Report for International Patent Application No. PCT/EP2011/064831, European Patent Office, Netherlands, mailed on Sep. 27, 2011.
International Search Report for International Patent Application No. PCT/EP2011/064833, European Patent Office, Netherlands, mailed on Sep. 30, 2011.
English Language Abstract of Japanese Patent Publication No. 10-251265 A, published Sep. 22, 1998, Japanese Patent Office Patent & Utility Model Gazette DB, Patent Abstract of Japan.
Office Action mailed Sep. 7, 2012, for U.S. Appl. No. 13/086,512, filed Apr. 14, 2011, inventors Himmler et al., U.S. Patent and Trademark Office, Alexandria, VA.
Notice of Allowance mailed Jan. 31, 2013, for U.S. Appl. No. 13/086,512, filed Apr. 14, 2011, inventors Himmler et al., U.S. Patent and Trademark Office, Alexandria, VA.
Draber, W., "Synthesis of 1,4-Dithiins from Maleimide Derivatives," *Chem Ber* 100:1559-1570, Wiley-VCH, Germany (1967).
Unverified English Translation of Polish Provisional Patent No. PL 143 804 B2, Polish People's Republic Patent Office of the PPR (1988).

* cited by examiner

*Primary Examiner* — Michael Barker
*Assistant Examiner* — Po-Chih Chen
(74) *Attorney, Agent, or Firm* — Sterne, Kessler, Goldstein & Fox PLLC

(57) ABSTRACT

The present invention relates to a new process for preparing dithiine-tetracarboximides.

14 Claims, No Drawings

PROCESS FOR PREPARING DITHIINE-TETRACARBOXIMIDES

The present invention relates to a new process for preparing dithiine-tetracarboximides.

Dithiine-tetracarboximides as such are already known. It is also known that these dithiine-tetracarboximides can be used as anthelmintics against internal parasites of animals, more particularly nematodes, and have insecticidal activity (cf. U.S. Pat. No. 3,364,229). It is known, furthermore, that certain dithiine-tetracarboximides possess antibacterial activity and have a certain activity against causative organisms of human mycoses (cf. Il Farmaco 2005, 60, 944-947). It is also known that dithiine-tetracarboximides can be used as pigments in electrophotographic photoreceptors or as dyes in paints and polymers (cf. JP-A 10-251265, PL-B 143804).

Dithiine-tetracarboximides of the formula (I)

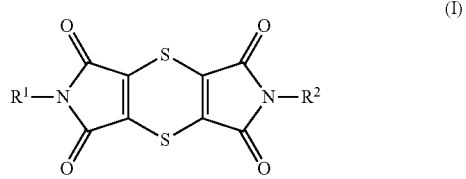

in which $R^1$ and $R^2$ are identical or different and are hydrogen, or are $C_1$-$C_8$-alkyl which is optionally substituted one or more times by halogen, —$OR^3$, and/or —$COR^4$, are $C_3$-$C_7$-cycloalkyl which is optionally substituted one or more times by halogen, $C_1$-$C_4$-alkyl or $C_1$-$C_4$-haloalkyl, or are aryl or aryl-($C_1$-$C_4$-alkyl) each of which is optionally substituted one or more times by halogen, $C_1$-$C_4$-alkyl, $C_1$-$C_4$-haloalkyl, —$COR^4$ or sulphonylamino, $R^3$ is hydrogen, $C_1$-$C_4$-alkyl or $C_1$-$C_4$-alkylcarbonyl or is aryl which is optionally substituted one or more times by halogen, $C_1$-$C_4$-alkyl or $C_1$-$C_4$-haloalkyl, $R^4$ is hydroxyl, $C_1$-$C_4$-alkyl or $C_1$-$C_4$-alkoxy, can be prepared in a variety of known ways.

For example, in one process (cf. U.S. Pat. No. 3,364,229; Chem. Ber. 1967, 100, 1559-1570), in a first stage, dichloromaleic anhydride of the formula (II) is reacted with an amine of the formula (III), optionally in the presence of a diluent. Subsequently, the resultant dichloromaleimides of the formula (IV) are then reacted with a sulphur compound (e.g. hydrogen sulphide or thiourea). The preparation of the dithiine-tetracarboximides of the formula (I) by this process can be illustrated by the following scheme:

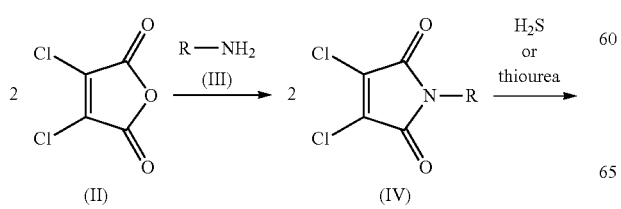

$R = R^1$ or $R^2$

This process has the disadvantage that, for example, operating with the highly toxic gaseous hydrogen sulphide is from a technical standpoint very difficult, costly and inconvenient. When thiourea is used, unwanted by-products are obtained along with the target product, and are very difficult to remove, and detract from the attainable yields (cf. J. Heterocycl. Chem. 1988, 25, 901-906).

In another process which has been disclosed (cf. Synthetic Communications 2006, 36, 3591-3597), in a first stage, succinic anhydride of the formula (V) is reacted with an amine of the formula (III), optionally in the presence of a diluent. Subsequently, the resultant succinic monoamides of the formula (VI) are reacted for 6 hours with a large excess of thionyl chloride in the presence of dioxane as diluent, at room temperature, to give, finally, in a sequence of numerous reaction steps, the dithiine-tetracarboximides of the formula (I). The dithiine-tetracarboximides are optionally isolated directly from the reaction mixture or by filtration following addition of water. Depending on reaction conditions (diluents) and the nature of the radicals R, it is possible in certain circumstances to isolate the dithiine-diisoimides of the formula (VII) before they are converted into the dithiine-tetracarboximides of the formula (I). This preparation method for the dithiine-tetracarboximides of the formula (I) can be illustrated by the following scheme:

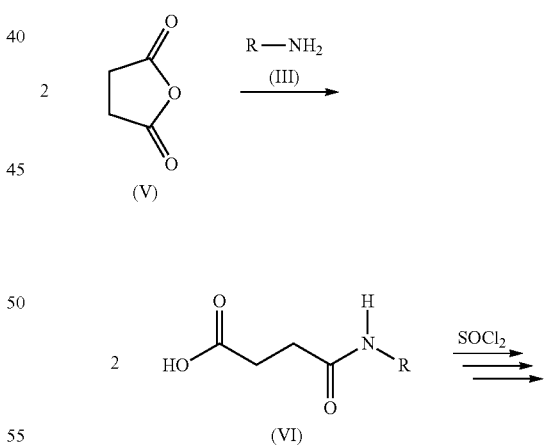

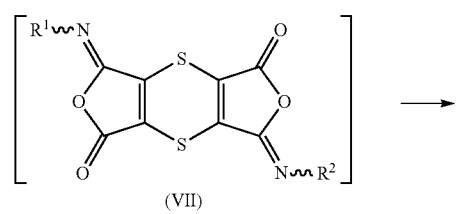

-continued

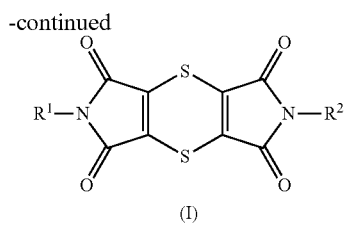

R = R¹ or R²

Disadvantages of this process are the long reaction time and also the outcome where either the yields obtained generally do not exceed about 30-40% of theory or else the purities of the isolated products are inadequate (see comparative examples). A further disadvantage, in the case of aqueous work-up of the reaction mixture, is that it involves destroying large amounts of thionyl chloride; the gases formed ($SO_2$ and HCl) have to be disposed of. Likewise a disadvantage is the fact that, from experience (see comparative examples), the product is not obtained in one fraction. Instead, it is frequently the case that, following initial isolation of product by filtration, further product precipitates from the filtrate after prolonged standing (overnight, for example), and must be isolated again by filtration. Occasionally this operation must be carried out once more. This procedure is very laborious and time-consuming.

Consequently there continues to be a need for a technically simple and economic preparation process for dithiine-tetracarboximides of the formula (I).

A new process has been found for preparing dithiine-tetracarboximides of the general formula (I)

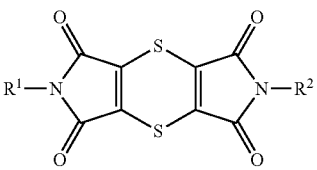

in which R¹ and R² have the definitions indicated above, characterized in that
in a first stage, succinic monoamides of the formula (VI)

(VI)

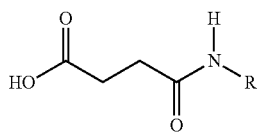

in which R is R¹ or R²
are reacted with an excess of thionyl chloride, optionally in the presence of a diluent,
then the excess of thionyl chloride is removed and the resulting product mixture is converted in a second stage, in a mixture of an organic solvent, water and a phase transfer catalyst into the dithiine-tetracarboximides of the formula (I).

In this way the dithiine-tetracarboximides of the formula (I) can be obtained in relatively high yield, a relatively short time, and relatively good purity. It is, moreover, possible to recover the organic solvent.

The product mixture obtained in the first step of the process of the invention also already includes dithiine-tetracarboximides of the formula (I), but its principal components are polysulphides of the formula (IX),

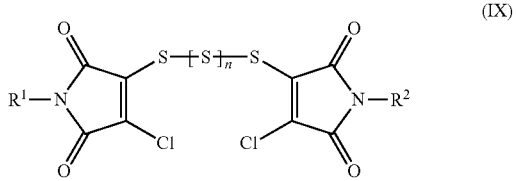

and also, depending on the work-up method, thiosulphonic acid derivatives of the formula (VIII)

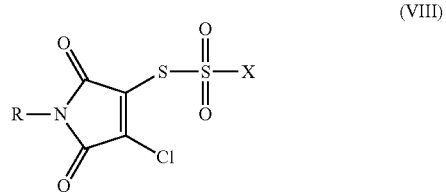

In the thiosulphonic acid derivatives of the general formula (VIII), R stands for the definitions of R¹ and R², indicated above, and X stands for chlorine or hydroxyl.

In the polysulphides of the general formula (IX), R¹ and R² stand for the definitions indicated above, and n stands for 0, 1, 2, 3, 4, 5, 6, 7 or 8.

Compounds of the general formula (VIII) are obtained, alongside other products, when the reaction mixture, following the reaction of the compounds of the general formula (VI) with thionyl chloride, is concentrated.

Compounds of the general formula (IX) are obtained, alongside other products, when the reaction mixture, following the reaction of the compounds of the general formula (VI) with thionyl chloride, is concentrated, dissolved in an inert, water-immiscible solvent such as methylene chloride, for example, and extracted by shaking with water at room temperature. Following removal of the organic phase, drying and concentrating, a mixture is obtained which in addition to dithiine-tetracarboximides of the formula (I) contains primarily compounds of the general formula (IX).

The process of the invention for preparing the dithiine-tetracarboximides of the formula (I) can be illustrated by the following scheme:

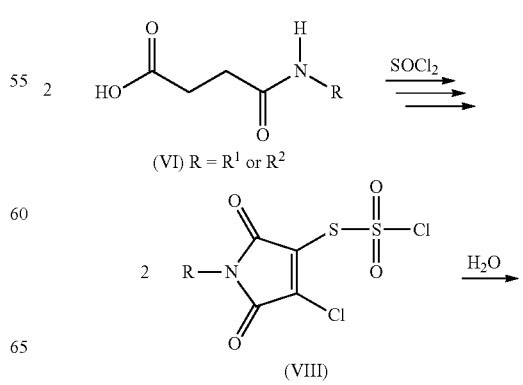

-continued

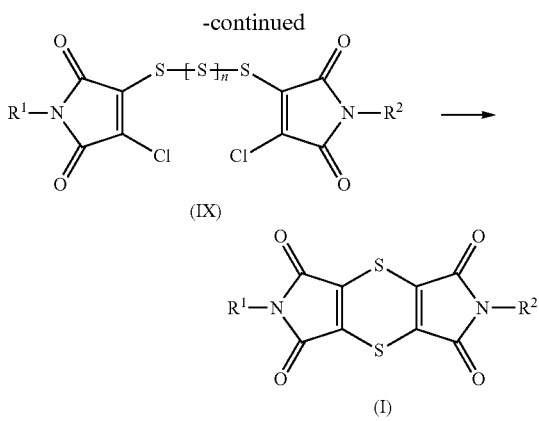

A general definition of the succinic monoamides used as starting materials when carrying out the process of the invention is provided by the formula (VI). R stands for the definitions of $R^1$ or $R^2$.

$R^1$ and $R^2$ preferably are identical or different and preferably are hydrogen, or are $C_1$-$C_6$-alkyl which is optionally substituted one or more times by fluorine, chlorine, bromine, —$OR^3$ and/or —$COR^4$, or are $C_3$-$C_7$-cycloalkyl which is optionally substituted one or more times by chlorine, methyl or trifluoromethyl, or are phenyl or phenyl-($C_1$-$C_4$-alkyl) each of which is optionally substituted one or more times by fluorine, chlorine, bromine, methyl, trifluoromethyl, —$COR^4$ and/or sulphonylamino.

$R^1$ and $R^2$ more preferably are identical or different and more preferably are hydrogen, or are $C_1$-$C_4$-alkyl which is optionally substituted one or more times by fluorine, chlorine, hydroxyl, methoxy, ethoxy, methylcarbonyloxy and/or carboxyl, or are $C_3$-$C_7$-cycloalkyl which is optionally substituted one or more times by chlorine, methyl or trifluoromethyl, or are phenyl, benzyl, 1-phenethyl, 2-phenethyl or 2-methyl-2-phenethyl each of which is optionally substituted one to three times by fluorine, chlorine, bromine, methyl, trifluoromethyl, —$COR^4$ and/or sulphonylamino.

$R^1$ and $R^2$ very preferably are identical or different and very preferably are hydrogen, methyl, ethyl, n-propyl, isopropyl, 2,2-difluoroethyl or 2,2,2-trifluoroethyl or are cyclopropyl or cyclohexyl each of which is optionally substituted by chlorine, methyl or trifluoromethyl.

$R^1$ and $R^2$ more particularly preferably are simultaneously methyl.

$R^3$ preferably is hydrogen, methyl, ethyl, methylcarbonyl or ethylcarbonyl or is phenyl which is optionally substituted one or more times by fluorine, chlorine, methyl, ethyl, n-propyl, isopropyl or trifluoromethyl.

$R^3$ more preferably is hydrogen, methyl, methylcarbonyl or phenyl.

$R^4$ preferably is hydroxyl, methyl, ethyl, methoxy or ethoxy.

$R^4$ more preferably is hydroxyl or methoxy.

As starting material it is particularly preferred to use N-methylsuccinamide, giving as the end product the compound (I-1) 2,6-dimethyl-1H,5H-[1,4]dithiino[2,3-c:5,6-c']dipyrrole-1,3,5,7(2H,6H)-tetrone.

If N-tert-butylsuccinamide is used as starting material, the end product obtained is the compound (I-2) 2,6-di-tert-butyl-1H,5H-[1,4]dithiino[2,3-c:5,6-c']dipyrrole-1,3,5,7(2H,6H)-tetrone.

If N-cyclohexylsuccinamide is used as starting material, the end product obtained is the compound (I-3) 2,6-dicyclohexyl-1H,5H[1,4]dithiino[2,3-c:5,6-c']pyrrole-1,3,5,7(2H,6H)-tetrone.

If N-propylsuccinamide is used as starting material, the end product obtained is the compound (I-4) 2,6-dipropyl-1H,5H-[1,4]dithiino[2,3-c:5,6-c']dipyrrole-1,3,5,7(2H,6H)-tetrone.

Intermediates obtained with particular preference are
(VIII-1) S-(4-chloro-1-methyl-2,5-dioxo-2,5-dihydro-1H-pyrrol-3-yl)chlorothiosulphate (R=Me, X=Cl),
(IX-1) 3,3'-trisulphane-1,3-diylbis(4-chloro-1-methyl-1H-pyrrole-2,5-dione) ($R^1$=$R^2$=Me, n=1)
(IX-2) 3,3'-disulphanediylbis(4-chloro-1-methyl-1H-pyrrole-2,5-dione) ($R^1$=$R^2$=Me, n=0)
(IX-3) 3,3'-disulphanediylbis(1-tert-butyl-4-chloro-1H-pyrrole-2,5-dione) ($R^1$=$R^2$=t-Bu, n=0)
(IX-4) 3,3'-trisulphane-1,3-diylbis(1-tert-butyl-4-chloro-1H-pyrrole-2,5-dione) ($R^1$=$R^2$=t-Bu, n=1)
(IX-5) 3,3'-trisulphane-1,3-diylbis(4-chloro-1-cyclohexyl-1H-pyrrole-2,5-dione) ($R^1$=$R^2$=cyclohexyl, n=1)

The amount of thionyl chloride in the first step of the process of the invention is between 2 and 100 mol per mole of succinic monoamide of the formula (VI). It is preferred to use between 4 and 50 mol, more preferably amounts of between 10 and 40 mol, per mole of succinic monoamide of the formula (VI).

The reaction temperature in the first step of the process of the invention can be varied within wide limits and is between 0° C. and 150° C. In order to obtain satisfactory space-time yields, it is preferred to operate at temperatures between 20° C. and 120° C., more preferably between 30° C. and 100° C.

The reaction time in the first step of the process of the invention is between 10 minutes and 24 hours. It is preferred to operate for between 30 minutes and 6 hours, more preferably between 1 and 4 hours.

The first step of the process of the invention can be carried out optionally in the presence of a diluent which as far as possible is inert under the reaction conditions. Such diluents include, by way of example, aliphatic hydrocarbons such as pentane, hexane, heptane, cyclohexane, methylcyclohexane, octane, isooctane, chlorinated hydrocarbons such as methylene chloride, chloroform, 1,2-dichloroethane, aromatic hydrocarbons such as toluene, xylene, mesitylene, ethylbenzene, anisol, chlorinated aromatic hydrocarbons such as chlorobenzene, dichlorobenzene, ethers such as diethyl ether, methyl tert-butyl ether, tetrahydrofuran, dioxane, nitriles such as acetonitrile, propionitrile, butyronitrile, esters such as methyl acetate and ethyl acetate. It is preferred to operate in toluene, xylene, mesitylene, ethylbenzene, chlorobenzene or 1,2-dichlorobenzene or without diluent.

The thionyl chloride can be removed in principle by hydrolysis with water. The thionyl chloride is removed preferably by distillation under reduced pressure.

The diluent optionally present may likewise be distilled off under reduced pressure and, if desired, be replaced by another solvent. Preferably, however, only the excess thionyl chloride is distilled off and then, after addition of water and phase transfer catalyst, the reaction is continued in the same solvent.

In the second step of the process of the invention, the residue that is obtained following removal of the excess thionyl chloride and optionally of the diluent is dissolved in a new diluent and, after addition of a phase transfer catalyst, by heating in this solvent, is converted into the dithiine-carboximides of the formula (I). The reaction mixture is preferably stirred during this procedure.

In the second step of the process of the invention, organic solvents or solvent mixtures are used. These solvents are preferably only slightly miscible with water.

Suitable diluents for the second step of the process of the invention include, specifically, hydrocarbons such as hexane, heptane, cyclohexane, methylcyclohexane, octane, isooctane, toluene, xylenes, mesitylene, ethylbenzene, chlorobenzene, dichlorobenzene, nitrobenzene, water or mixtures of these diluents.

Preference is given to using hexane, heptane, cyclohexane, methylcyclohexane, octane, isooctane, toluene, xylenes, mesitylene, chlorobenzene, dichlorobenzene, water or mixtures of these diluents.

Very particular preference is given to using mixtures of water and toluene, xylene or chlorobenzene.

The mixing ratio of water to organic solvent here may be varied within wide limits of, for example, 9:1 to 1:9.

As phase transfer catalysts (PTC) it is possible in principle to use all compounds with a known activity as PTC. Such compounds may be, for example, phase transfer catalysts from the series of the quaternary ammonium salts or of the quaternary phosphonium salts.

This phase transfer catalyst preferably possesses the general formula (X)

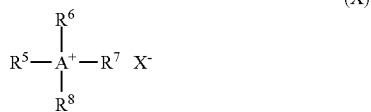

(X)

in which
R$^5$, R$^6$, R$^7$ and R$^8$ independently of one another are identical or different and are each straight-chain or branched C$_1$-C$_{28}$-alkyl, C$_6$-C$_{10}$-aryl or benzyl,
X is halogen, hydrogen sulphate, sulphate, dihydrogen phosphate, hydrogen phosphate, phosphate or acetate (preferably bromine, chlorine, fluorine, hydrogen sulphate, sulphate, phosphate and acetate),
A is N or P.

Examples that may be given of such phase transfer catalysts include tetrabutylammonium fluoride, chloride, bromide, iodide, acetate and hydrogen sulphate, tetraethylammonium bromide and iodide, methyltributylammonium chloride, bromide, iodide, acetate and hydrogen sulphate, benzyldodecyldimethylammonium chloride and bromide, benzyltriethylammonium bromide and chloride, dodecyltrimethylammonium chloride and bromide, tetradecyltrimethylammonium chloride and bromide, methyltrioctylammonium chloride, methyltridecylammonium chloride, tetraoctylammonium bromide and chloride, didecyldimethylammonium chloride and bromide, tetraphenylphosphonium bromide, ethyltriphenylphosphonium bromide, ethyltriphenylphosphonium iodide and ethyltriphenylphosphonium acetate.

In addition it is also possible for phase transfer catalysts such as 4-dialkylaminopyridinium salts or hexaalkylguanidinium salts to be employed.

Preference is given to using methyltrioctylammonium chloride (trade name Aliquat® 336; present in a mixture with methyltridecylammonium chloride), methyltridecylammonium chloride or bromide, tetraoctylammonium bromide or chloride, dodecyltrimethylammonium chloride or bromide, tetradecyltrimethylammonium chloride or bromide, didecyldimethylammonium chloride or bromide and benzyldodecyldimethylammonium chloride or bromide for use as phase transfer catalysts.

The amount of phase transfer catalyst in the process of the invention can be varied within wide limits. The amount is preferably between 0.1 and 10 mol percent, based on the succinimide of the formula (VI), more preferably between 1 and 7 mol percent, based on the succinimide of the formula (VI).

In a further embodiment of the process it is possible for the filtrate which is obtained after the isolation of the product of the general formula (I) by filtration and which is two-phase when—as preferred—a mixture is used of water and an organic diluent which is immiscible or only a little miscible with water, to be employed in the next batch for carrying out the second step of the process of the invention. This can be repeated a number of times, preferably up to ten times, more preferably up to five times. As a result, not only is the use of the phase transfer catalyst significantly reduced, relative to succinimide of the general formula (VI), but also, at the same time, the required amounts of organic diluent and water are significantly reduced, and this makes the process even more economical.

Depending on which phase transfer catalyst is used, it is also possible for only the organic phase, after removal of the desired product, to be re-used.

The reaction temperature in the second step of the process of the invention can be varied within wide limits and is between 0° C. and 200° C. It is preferred to operate at temperatures between 20° C. and 150° C., more preferably between 30° C. and 130° C.

The reaction time in the second step of the process of the invention is between 5 minutes and 24 hours. It is preferred to operate for between 30 minutes and 12 hours, more preferably between 1 and 8 hours.

The process of the invention is illustrated by, but not confined to, the following examples.

EXAMPLE 1

N-methylsuccinimide [5.24 g; 40 mmol] was introduced and 23.8 g [200 mmol] of thionyl chloride were added dropwise with stirring at 5° C. The resulting solution was then introduced dropwise over the course of about 20 minutes into 23.8 g [200 mmol] of thionyl chloride which had been heated to 60° C. The mixture was subsequently heated to 80° C. and stirred at this temperature for 1 hour. The reaction mixture was concentrated on a rotary evaporator. This gave 9.3 g of a thick brown oil which according to HPLC and LC/MS analysis contains 11.1 area-percent of compound (VIII-1), 26.3 area-percent of compound (I-1), 5.8 area-percent of compound (IX-1, n=0) and 24.7 area-percent of compound (IX-1, n=1).

This oil was dissolved in 30 ml of toluene, 0.2 g of Aliquat® 336 was added, and then 10 ml of water were added dropwise. This mixture was heated with thorough stirring at 80° C. for 4 hours. Thereafter it was cooled to room temperature, and the precipitated solid was isolated by suction filtration, washed with water and ethanol, and dried. This gave 3.10 g of black solid, which according to HPLC analysis is composed to an extent of 99.3 area-percent of compound (I-1), corresponding to a yield of 54.5% of theory.

EXAMPLE 2

The procedure of example 1 was repeated, but adding 0.4 g of a 50% strength aqueous solution of benzyldodecyldimethylammonium chloride (Zephirol®) as phase transfer catalyst. This gave 3.27 g of black solid which according to HPLC analysis is composed to an extent of 99.1 area-percent of compound (I-1), corresponding to a yield of 57.4% of theory.

EXAMPLE 3

The procedure of example 1 was repeated, but adding 0.2 g of dodecyltrimethylammonium bromide as phase transfer catalyst. This gave 2.30 g of black solid which according to HPLC analysis is composed to an extent of 99.0 area-percent of compound (I-1), corresponding to a yield of 40.3% of theory.

EXAMPLE 4

The procedure of example 1 was repeated, but adding 0.2 g of tetradecyltrimethylammonium bromide as phase transfer catalyst. This gave 2.43 g of black solid which according to HPLC analysis is composed to an extent of 99.2 area-percent of compound (I-1), corresponding to a yield of 42.7% of theory.

EXAMPLE 5

The procedure of example 1 was repeated, but adding 0.2 g of tetraoctylammonium bromide as phase transfer catalyst. This gave 2.84 g of black solid which according to HPLC analysis is composed to an extent of 99.5 area-percent of compound (I-1), corresponding to a yield of 50.0% of theory.

EXAMPLE 6

The procedure of example 1 was repeated, but adding 0.4 g of a 50% strength aqueous solution of didecyldimethylammonium chloride as phase transfer catalyst. This gave 3.45 g of black solid which according to HPLC analysis is composed to an extent of 99.1 area-percent of compound (I-1), corresponding to a yield of 60.6% of theory.

EXAMPLE 7

N-methylsuccinimide [15.74 g; 120 mmol] as a suspension in 49 ml of toluene was introduced and 24.9 g [209 mmol] of thionyl chloride were added dropwise with stirring at 10-20° C. This gave a two-phase solution, of which the bottom phase was separated off and introduced dropwise over the course of about 60 minutes into 132.1 g [1110 mmol] of thionyl chloride which had been heated to 60° C. The mixture was subsequently heated to about 80° C. and stirred at this temperature for 1 hour. The reaction mixture was subsequently concentrated on a rotary evaporator. This gave 29.37 g of a thick brown oil which according to HPLC analysis contains 5.0 area-percent of compound (VIII-1), 14.5 area-percent of compound (I-1), 19.5 area-percent of compound (IX-1, n=0) and 26.9 area-percent of compound (IX-1, n=1).

This oil was dissolved in 90 ml of toluene, 0.6 g of Aliquat® 336 was added, and then 30 ml of water were added dropwise. This mixture was heated with thorough stirring at reflux (85-88° C.) for 4 hours. Thereafter it was cooled to room temperature, and the precipitated solid was isolated by suction filtration, washed with 30 ml of water and with twice 30 ml of ethanol, and dried. This gave 11.10 g of black solid, which according to HPLC analysis is composed to an extent of 98.9 area-percent of compound (I-1), corresponding to a yield of 64.8% of theory.

COMPARATIVE EXAMPLE 1

N-methylsuccinimide [5.24 g; 40 mmol] was introduced and 23.8 g [200 mmol] of thionyl chloride were added dropwise with stirring at 5° C. The resulting solution was then introduced dropwise over the course of about 20 minutes into 23.8 g [200 mmol] of thionyl chloride which had been heated to 60° C. The mixture was subsequently heated to 80° C. and stirred at this temperature for 1 hour. The reaction mixture was concentrated on a rotary evaporator. This gave 10.3 g of a thick brown oil which according to HPLC and LC/MS analysis contains 6.6 area-percent of compound (VIII-1), 19 area-percent of compound (I-1), 16.6 area-percent of compound (IX-1, n=0) and 34.1 area-percent of compound (IX-1, n=1).

This oil was dissolved in 30 ml of toluene and then, without addition of a phase transfer catalyst, 10 ml of water were added dropwise. This mixture was heated with thorough stirring at 80° C. for 4 hours. Thereafter it was cooled to room temperature, and the precipitated solid was isolated by suction filtration, washed with water and ethanol, and dried. This gave 0.90 g of dark green solid, which according to HPLC analysis is composed to an extent of 98.6 area-percent of compound (I-1), corresponding to a yield of 15.7% of theory.

EXAMPLE 8

N-methylsuccinimide [5.24 g; 40 mmol] was introduced and 23.8 g [200 mmol] of thionyl chloride were added dropwise with stirring at 5° C. The resulting solution was then introduced dropwise over the course of about 20 minutes into 23.8 g [200 mmol] of thionyl chloride which had been heated to 60° C. The mixture was subsequently heated to 80° C. and stirred at this temperature for 1 hour. The reaction mixture was concentrated on a rotary evaporator. This gave 9.7 g of a thick brown oil which according to HPLC analysis contains 4.2 area-percent of compound (VIII-1), 15.3 area-percent of compound (I-1), 20.1 area-percent of compound (IX-1, n=0) and 28.3 area-percent of compound (IX-1, n=1).

This oil was dissolved in 30 ml of toluene, 0.1 g of Aliquat® 336 was added, and then 10 ml of water were added dropwise. This mixture was heated with thorough stirring at reflux (about 94-97° C.) for 4 hours. Thereafter it was cooled to room temperature, and the precipitated solid was isolated by suction filtration, washed with water and ethanol, and dried. This gave 3.29 g of black solid, which according to HPLC analysis is composed to an extent of 99.4 area-percent of compound (I-1), corresponding to a yield of 57.9% of theory.

EXAMPLE 9

The procedure of example 8 was repeated, but adding 0.2 g of tetraoctylammonium bromide as phase transfer catalyst. This gave 3.47 g of black solid which according to HPLC analysis is composed to an extent of 98.7 area-percent of compound (I-1), corresponding to a yield of 60.7% of theory.

COMPARATIVE EXAMPLE 2

N-methylsuccinimide [5.24 g; 40 mmol] was introduced and 23.8 g [200 mmol] of thionyl chloride were added dropwise with stirring at 5° C. The resulting solution was then introduced dropwise over the course of about 20 minutes into 23.8 g [200 mmol] of thionyl chloride which had been heated to 60° C. The mixture was subsequently heated to 80° C. and stirred at this temperature for 1 hour. The reaction mixture was concentrated on a rotary evaporator. This gave 9.5 g of a thick brown oil which according to HPLC analysis contains 7 area-percent of compound (VIII-1), 18.5 area-percent of compound (I-1), 17.6 area-percent of compound (IX-1, n=0) and 30 area-percent of compound (IX-1, n=1).

This oil was dissolved in 30 ml of chlorobenzene and then, without addition of a phase transfer catalyst, 10 ml of water were added dropwise. This mixture was heated with thorough stirring at 80° C. for 4 hours. Thereafter it was cooled to room temperature, and the precipitated solid was isolated by suction filtration, washed with water and ethanol, and dried. This gave 1.12 g of black solid, which according to HPLC analysis is composed to an extent of 98.8 area-percent of compound (I-1), corresponding to a yield of 19.6% of theory.

EXAMPLE 10

N-methylsuccinimide [26.23 g; 200 mmol] in 35.3 g of toluene was introduced and 42.35 g [356 mmol] of thionyl chloride were added dropwise with stirring at 5-10° C. The solution which resulted at room temperature was then introduced dropwise over the course of 2 hours into 225 g [1890 mmol] of thionyl chloride which had been heated to 60° C. The mixture was then heated to 80° C. and stirred at this temperature for 1 hour. The reaction mixture was subsequently concentrated on a rotary evaporator to a bath temperature of 70° C. and to 25 mbar. This gave 43.7 g of suspension as a residue. The 43.7 g of residue, still hot, were dissolved in 174 g of toluene, 4.05 g of Aliquat® 336 were added, and then 55 ml of water were added dropwise over the course of about 5 minutes, beginning at about 55° C. Subsequently, with thorough stirring, the mixture was heated at 80° C. for 4 hours. It was then left to cool to room temperature, and the precipitated solid was isolated by suction filtration, washed with 55 ml of water and with twice 55 ml of ethanol, and dried. This gave 20.36 g of black solid, which according to HPLC analysis is composed to an extent of 98.6 area-percent of compound (I-1), corresponding to a yield of 71.1% of theory.

EXAMPLE 11

N-methylsuccinimide [8 g; 61 mmol] in 13.4 g of chlorobenzene was introduced and 12.57 g [106 mmol] of thionyl chloride were added dropwise with stirring at 5-10° C. The solution which resulted at room temperature was then introduced dropwise over the course of 1 hour into 66.6 g [560 mmol] of thionyl chloride which had been heated to 60° C. The mixture was then heated to 80° C. and stirred at this temperature for 1 hour. The reaction mixture was subsequently concentrated on a rotary evaporator. The residue, still hot, was dissolved in 79 g of toluene. 2.4 g of Aliquat® 336 (about 9.7 mol percent, based on N-methylsuccinimide) were added, and then 31 ml of water were added dropwise. Subsequently, with thorough stirring, the mixture was heated at 75° C. for 4 hours. It was then left to cool to room temperature, and the precipitated solid was isolated by suction filtration, washed with 30 ml of water and then with 30 ml of ethanol, and dried. This gave 6.4 g of solid, which according to HPLC analysis is composed to an extent of 98 area-percent of compound (I-1), corresponding to a yield of 73% of theory, and 115 g of two-phase filtrate.

EXAMPLE 12

N-methylsuccinimide [8 g; 61 mmol] in 13.4 g of chlorobenzene was introduced and 12.57 g [106 mmol] of thionyl chloride were added dropwise with stirring at 5-10° C. The solution which resulted at room temperature was then introduced dropwise over the course of 1 hour into 66.6 g [560 mmol] of thionyl chloride which had been heated to 60° C. The mixture was then heated to 80° C. and stirred at this temperature for 1 hour. The reaction mixture was then concentrated on a rotary evaporator. The residue, while still hot, was admixed dropwise with the filtrate from Example 11. The mixture was then heated with thorough stirring at 75° C. for 4 hours. It was then allowed to cool to room temperature, and the precipitated solid was isolated by suction filtration, washed with 30 ml of water and then with 30 ml of ethanol, and dried. This gave 6.7 g of solid, which according to HPLC analysis is composed to an extent of 97.7 area-percent of compound (I-1), corresponding to a yield of 76% of theory, and 114 g of filtrate.

EXAMPLE 13

N-methylsuccinimide [8 g; 61 mmol] in 13.4 g of chlorobenzene was introduced and 12.57 g [106 mmol] of thionyl chloride were added dropwise with stirring at 5-10° C. The solution which resulted at room temperature was then introduced dropwise over the course of 1 hour into 66.6 g [560 mmol] of thionyl chloride which had been heated to 60° C. The mixture was then heated to 80° C. and stirred at this temperature for 1 hour. The reaction mixture was then concentrated on a rotary evaporator. The residue, while still hot, was admixed dropwise with the filtrate from Example 12. The mixture was then heated with thorough stirring at 75° C. for 4 hours. It was then allowed to cool to room temperature, and the precipitated solid was isolated by suction filtration, washed with 30 ml of water and then with 30 ml of ethanol, and dried. This gave 6.5 g of solid, which according to HPLC analysis is composed to an extent of 98.1 area-percent of compound (I-1), corresponding to a yield of 74% of theory, and 119 g of filtrate.

EXAMPLE 14

N-methylsuccinimide [8 g; 61 mmol] in 13.4 g of chlorobenzene was introduced and 12.57 g [106 mmol] of thionyl chloride were added dropwise with stirring at 5-10° C. The solution which resulted at room temperature was then introduced dropwise over the course of 1 hour into 66.6 g [560 mmol] of thionyl chloride which had been heated to 60° C. The mixture was then heated to 80° C. and stirred at this temperature for 1 hour. The reaction mixture was then concentrated on a rotary evaporator. The residue, while still hot, was admixed dropwise with the filtrate from Example 13. The mixture was then heated with thorough stirring at 75° C. for 4 hours. It was then allowed to cool to room temperature, and the precipitated solid was isolated by suction filtration, washed with 30 ml of water and then with 30 ml of ethanol, and dried. This gave 6.3 g of solid, which according to HPLC analysis is composed to an extent of 98 area-percent of compound (I-1), corresponding to a yield of 72% of theory, and 114 g of filtrate.

EXAMPLE 15

N-methylsuccinimide [8 g; 61 mmol] in 13.4 g of chlorobenzene was introduced and 12.57 g [106 mmol] of thionyl chloride were added dropwise with stirring at 5-10° C. The solution which resulted at room temperature was then introduced dropwise over the course of 1 hour into 66.6 g [560 mmol] of thionyl chloride which had been heated to 60° C. The mixture was then heated to 80° C. and stirred at this temperature for 1 hour. The reaction mixture was then concentrated on a rotary evaporator. The residue, while still hot, was admixed dropwise with the filtrate from Example 14. The mixture was then heated with thorough stirring at 75° C. for 4 hours. It was then allowed to cool to room temperature, and the precipitated solid was isolated by suction filtration, washed with 30 ml of water and then with 30 ml of ethanol, and dried. This gave 6.4 g of solid, which according to HPLC analysis is composed to an extent of 98.8 area-percent of compound (I-1), corresponding to a yield of 73% of theory.

General Information:

HPLC conditions: Zorbax Eclipse Plus C18 4.6*50 mm 1.8 μm, eluent A: 0.1% $H_3PO_4$, eluent B: acetonitrile, gradient: 90/10, 20%/min, 5/95 (1.75), flow rate: 2 ml/min, 55° C.

The invention claimed is:

1. A process for preparing a compound of formula (I)

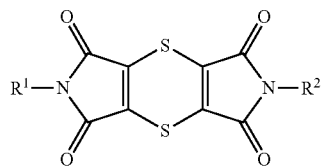

in which
- $R^1$ and $R^2$ are identical or different and are hydrogen, or are $C_1$-$C_8$-alkyl which is optionally substituted with one or more halogen, —$OR^3$, and/or —$COR^4$, are $C_3$-$C_7$-cycloalkyl which is optionally substituted with one or more halogen, $C_1$-$C_4$-alkyl or $C_1$-$C_4$-haloalkyl, or are aryl or aryl-($C_1$-$C_4$-alkyl) each of which is optionally substituted with one or more halogen, $C_1$-$C_1$-$C_4$-haloalkyl, —$COR^4$ or sulphonylamino,
- $R^3$ is hydrogen, $C_1$-$C_4$-alkyl or $C_1$-$C_4$-alkylcarbonyl or is aryl which is optionally substituted with one or more halogen, $C_1$-$C_4$-alkyl or $C_1$-$C_4$-haloalkyl,
- $R^4$ is hydroxyl, $C_1$-$C_4$-alkyl or $C_1$-$C_4$-alkoxy , comprising:

(1) reacting a succinic monoamide of formula (VI)

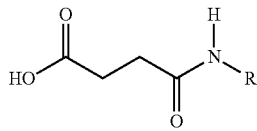

in which R is $R^1$ or $R^2$ with an excess of thionyl chloride, optionally in the presence of a diluent, (2) removing thionyl chloride to form a first product mixture; and (3) adding an organic solvent, water and a phase transfer catalyst to the first product mixture and after a reaction time of between 5 minutes and 24 hours converting, into a second product mixture comprising a compound of formula (I), wherein the phase transfer catalyst is selected from the group consisting of tetrabutylammonium bromide, tetrabutylammonium hydrogen sulphate, benzyldodecyldimethylammonium chloride, dodecyltrimethylammonium chloride, dodecyltrimethylammonium bromide, tetradecyltrimethylammonium bromide, methyltrioctylammonium chloride, methyltridecylammonium chloride, a mixture of methyltrioctylammonium chloride and methyltridecylammonium chloride, tetraoctylammonium bromide, and didecyldimethylammonium chloride.

2. The process according to claim 1, wherein the phase transfer catalyst is selected from the group consisting of tetrabutylammonium hydrogen sulphate, benzyldodecyldimethylammonium chloride, dodecyltrimethylammonium chloride, tetradecyltrimethylammonium bromide, a mixture of methyltrioctylammonium chloride and methyltridecylammonium chloride, tetraoctylammonium bromide, didecyldimethylammonium chloride.

3. The process according to claim 1, wherein the organic solvent in (3) is selected from the group consisting of hexane, heptane, cyclohexane, methylcyclohexane, octane, isooctane, toluene, xylenes, mesitylene, ethylbenzene, chlorobenzene, dichlorobenzene, nitrobenzene, and mixtures thereof.

4. The process of claim 1, further comprising:
(4) filtering the second product mixture of (3) to separate the compound of formula (I) from filtrate.

5. The process of claim 4, wherein an organic solvent, water, and a phase transfer catalyst is added to the filtrate obtained in (4) and after a reaction time of between 5 minutes and 24 hours is converted into a compound of formula (I).

6. The process according to claim 5, wherein the filtrate is used again up to ten times.

7. The process according to claim 5 or 6, wherein only the organic phase, following removal of the desired product, is re-used.

8. The process of claim 1, wherein in (1), between 4 and 50 moles of thionyl chloride are used per mole of the succinic monoamide of formula (VI).

9. The process of claim 1, wherein in (1), between 10 and 40 moles of thionyl chloride are used per mole of the succinic monoamide of formula (VI).

10. The process of claim 1, wherein the succinic monoamide is N-methylsuccinamide, N-butylsuccinamide, N-cyclohexylsuccinamide, or N-propylsuccinamide.

11. The process of claim 1, wherein the compound of formula (I) is selected from:
- 2,6-dimethyl-1H,5H-[1,4]dithiino[2,3-c:5,6-c']dipyrrole-1,3,5,7(2H,6H)-tetrone;
- 2,6-di-tert-butyl-1H,5H-[1,4]dithiino[2,3-c:5,6-c']dipyrrole-1,3,5,7(2H,6H)-tetrone;
- 2,6-dicyclohexyl-1H,5H-[1,4]dithiino[2,3-c:5,6-c']dipyrrole-1,3,5,7(2H,6H)-tetrone; or 2,6-dipropyl-1H,5H-[1,4]dithiino[2,3-c:5,6-c']dipyrrole-1,3,5,7(2H,6H)-tetrone.

12. The process of claim 1, wherein the thionyl chloride is removed by distillation.

13. The process of claim 1, wherein (3) is carried out at a temperature between 30 ° C. and 130 ° C.

14. The process of claim 1, wherein in (3) the reaction time is between 30 minutes and 6 hours.

* * * * *